United States Patent [19]

Rafferty et al.

[11] Patent Number: 5,002,703

[45] Date of Patent: Mar. 26, 1991

[54] BENZOIC ACID AND BENZOIC ACID ESTER DERIVATIVES HAVING ANTIINFLAMMATORY AND ANALGESIC ACTIVITY

[75] Inventors: Michael F. Rafferty; Graham Johnson, both of Ann Arbor, Mich.

[73] Assignee: Warner-Lambert Company, Morris Plains, N.J.

[21] Appl. No.: 929,038

[22] Filed: Nov. 10, 1986

Related U.S. Application Data

[62] Division of Ser. No. 811,567, Dec. 20, 1985, Pat. No. 4,689,182.

[51] Int. Cl.$^5$ ............................................. C07C 311/03
[52] U.S. Cl. ..................................... 260/401; 560/12; 560/13; 562/430

[58] Field of Search .................. 260/402, 401; 560/12, 560/13; 562/430; 514/533, 538, 539, 558, 562

[56] References Cited

U.S. PATENT DOCUMENTS 4,447,477  4/1984  Witte et al. ............................ 560/12

*Primary Examiner*—Charles F. Warren
*Attorney, Agent, or Firm*—Joan Thierstein

[57] ABSTRACT

Novel benzoic acid or benzoic acid ester derivatives, pharmaceutical compositions and methods of use thereof are the present invention. Utility is for the treatment of arthritis, asthma, Raynaud's disease, inflammatory bowel disorders, trigeminal or herpetic neuralgia, inflammatory eye disorders, psoriasis, dental pain, and headaches, particularly vascular headache, such as migraine, cluster, mixed vascular syndromes, as well as nonvascular, tension headaches.

2 Claims, No Drawings

BENZOIC ACID AND BENZOIC ACID ESTER DERIVATIVES HAVING ANTIINFLAMMATORY AND ANALGESIC ACTIVITY

This is a divisional of the U.S. application Ser. No. 811,567 filed Dec. 20, 1985, now U.S. Pat. No. 4,689,182, issued Aug. 25, 1987.

BACKGROUND OF THE PRESENT INVENTION

The present invention is novel compounds, which are derivatives of benzoic acid and benzoic acid esters—having antiinflammatory activity for the treatment of arthritis, asthma, Raynaud's disease, inflammatory bowel disorders, trigeminal or herpetic neuralgia, inflammatory eye disorders, psoriasis, and/or having analgesic activity for the treatment of dental pain and headache, particularly vascular headache, such as migraine, cluster, and mixed vascular syndromes, as well as nonvascular, tension headache. Thus, the present invention is also a pharmaceutical composition comprising the novel compounds together with a pharmaceutically acceptable carrier or methods of use of such compounds for treatment of the above noted conditions.

Among known compounds are benzoic acid derivations in which the derivative is limited to a substituent having a (naphthoxy)isobutyramido containing group and for which compounds an antiphlogistic activity is disclosed. See U.S. Pat. No. 4,183,954. Additionally O. Exner, et al. discloses N-(4-carboxybenzyl)acetamide in "Quantitative Evaluation of the Inductive Effect," Coll. Czech. Chem. Commun. 27, 2299 (1962). But no teaching to activity or utility for the compound is indicated by Exner, et al.

Compounds related to capsaicin are disclosed in a series of patents. The compounds are thus not benzoic acid derivatives but have various amido, sulfonylamido or amidosulfonyl and thioamido linkages in combination with a benzyl or a benzyl analog moiety. Such compounds are found in U.S. Pat. No. 4,313,958, that claims the use of capsaicin; U.S. Pat. No. 4,460,602; U.S. Pat. No. 4,401,663; European Patent Application No. 0,132,113; U.S. Pat. No. 4,424,203; European Patent Application 0,132,114; European Patent Application 0,132,346 and European Patent Application 0,132,115 as well as European Patent Application 0,149,544 and 0,149,545. Of these European Patent Applications 0,132,115; 0,132,346; 0,132,114; 0,132,115, 0,149,544 and 0,149,545 include a short chain acyl group on the benzyl moiety. U.S. Pat. No. 3,992,540 discloses 3-quinolinecarboxamides. Analgesia is disclosed as an activity for the compounds of the references. However, none of the references teach the compounds having the moieties such as benzoic acid moities and their substituents, or particularly the combination of moieties, of the present invention.

DETAILED DESCRIPTION OF INVENTION

The novel compounds of the present invention have the following structural formula:

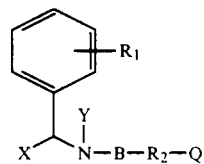

wherein:
(a) $R_1$ is tetrazolyl or COOR' wherein R' is H or lower alkyl of 1 to 4 carbons, inclusive;
(b) B is

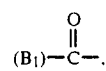

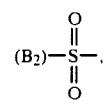

or

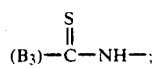

(c) X and Y are independently H or lower alkyl of 1 to 4 carbons, inclusive;
(d) $R_2$ is alkylene, alkenylene, alkynylene branched or linear chains of 1 to 11 carbons, inclusive;
(e) Q is $CH_3$, COOH, Br, $NH_2$, H, imidazolyl, cyclohexyl,

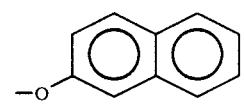

or

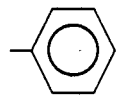

and nontoxic, pharmaceutically acceptable base or acid addition salts thereof, with the proviso that when B is ($B_1$) and Q is H, then $R_2$ is not methylene.

The term "lower alkyl of 1 to 4 carbons" means a straight or branched hydrocarbon chain up to 4 carbon atoms such as methyl, ethyl, propyl, isopropyl, butyl, isobutyl, secondary butyl or tertiary butyl.

The terms alkylene, alkenylene and alkynylene are divalent hydrocarbon straight or branched chains containing one or more single, double or triple carbon to carbon bonds, respectively.

Preferred embodiments of the present invention contain COOH as shown in the following formula (II):

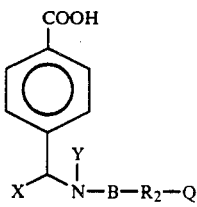

wherein X, Y, B, R₂ and Q are all as defined above. More preferred embodiments of the present invention are compounds of formula II wherein B is B₁ and X, Y, R₂ and Q are as defined above. The most preferred embodiment of the present invention is the compound N-(4-carboxybenzyl)nonanamide. The preferred method of use is for treating headaches, particularly migraines.

Examples of suitable acids for the preparation of the acid addition salts are inorganic acids such as hydrochloric acid, hydrobromic acid, sulfuric acid, phosphoric acid, and the like, and organic acids such as acetic acid, benzoic acid, tartaric acid, fumaric acid, succinic acid, maleic acid, arginine acid, lactic acid, tartaric acid, and sulfonic acids such as methansulfonic acid, ethansulfonic acid, benzenesulfonic acid or p-toluenesulfonic acid.

The base salts of the present inventions include those safe for topical or systemic administration, such as sodium, potassium, calcium, magnesium, and ammonium salts or the like.

Generally, the preparation of the compounds of the present invention is represented by the following scheme:

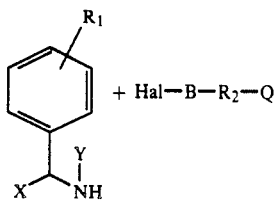

wherein R₁, X, Y, B, R Q are as defined above and Hal is chloro, bromo, or iodo, but preferably chloro.

The preparation uses standard synthetic techniques used in the examples or analogous to those used in the examples hereinafter. The starting materials for the preparation are readily available, known or can be prepared by known methods. The compositions containing the compounds of the formula (I')

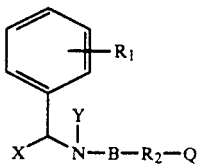

wherein:
(a) R₁ is tetrazolyl or COOR' wherein R' is H or lower alkyl of 1 to 4 carbons, inclusive; (b) B is

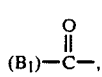

-continued

or

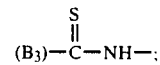

(c) X and Y are independently H or lower alkyl or 1 to 4 carbons, inclusive;
(d) R₂ is alkylene, alkenylene, alkynylene branched or linear chains of 1 to 11 carbons, inclusive;
(e) Q is CH₃, COOH, Br, NH₂, H, imidazolyl, cyclohexyl,

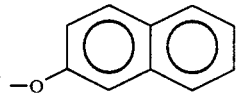

or

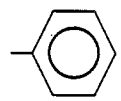

and nontoxic, pharmaceutically acceptable base of acid addition salts thereof, are comprised of an analgesic or antiinflammatory effective amount of a compound of formula I' as defined above or their pharmaceutically acceptable base or acid addition salts and a pharmaceutically acceptable carrier. Such compositions may be one of a broad range of known forms for topical or systemic administration.

The methods of use are for the treatment in mammals, particularly in humans, of various conditions such as enumerated above either for diseases known as inflammatory or for pain. An ordinarily skilled physician would recognize such conditions. The compounds of formula I are active in animal tests which are generally recognized as predictive for antiinflammatory or analgesic activity. Regardless of the route of administration selected, the compounds of the present invention are formulated into pharmaceutically acceptable dosage forms by conventional methods known to the pharmaceutical art. In general a preferred method of administration is, however, by oral dosage forms.

The compounds can be administered in such unit oral dosage forms as tablets, capsules, pills, powders, or granules. They may also be administered rectally or vaginally in such forms as suppositories or bougies. They may also be introduced parenterally, (e.g., subcutaneously, intravenously, or intramuscularly), using forms known to the pharmaceutical art.

An effective but nontoxic amount of the compound of formula I or the salts thereof is employed in treatment. The dosage regimen for treating inflammation or pain by the compounds of formula I and their salts as described above is selected in accordance with a variety of factors including the type, age, weight, sex, and medical condition of the subject, the severity of the inflammation or pain, the route of administration and the particular compound employed. Determination of the proper dosage for a particular situation is within the skill of the art. Generally, treatment is initiated with smaller dosages which are less than the optimum dose of the compound Thereafter the dosage is increased by small increments until the optimum effect under the circumstances is reached. For convenience, the total daily dosage may be divided and administered in portions during the day if desired.

Initial dosages of the compounds of the invention are ordinarily in the area of 1 mg/kg up to at least 100 mg/kg per dose orally, preferably 30 to 100 mg/kg orally are given. Each dose is given from one to four times daily or as needed. When other forms of administration are employed equivalent doses are administered.

An illustrative example of the activity for use as described above for the novel compounds of the present invention is an $ED_{50}$ of 33.03 mg/kg for the compound of Example 1 described in the following material when administered in a test based on that of Koster et al. [Fed. Proc., Vol. 18 (1959), p. 412] in which the peritoneal injection of acetic acid to mice provokes repeated stretching and twisting movements which persist for more than 6 hrs. Analgesics prevent or suppress these syndromes which are considered to be an exteriorization of a diffuse abdominal pain. A 1% solution of acetic acid in water is used at a dose of 0.01 ml/g or 100 mg/kg of acetic acid to release the syndrome.

The Example 1 compound is subcutaneously administered 30 minutes before the acetic acid injection and the mice are fasted 24 hrs before the start of the test. The stretching for the mice is observed and totaled for each mouse in a 15 minute observation period starting just after the acetic acid injection. The results are expressed as mg/kg which amount produces the desired inhibition of stretching or "writhing" in 50 percent of a population.

Additionally, the same Example 1 compound was effective at a dose of 100 mg/kg administered i.p. in reducing the inflammatory response to an injection of carrageenan into the rat foot pad. This is a commonly employed standard assay for the identification of antiinflammatory activity, based on the method described by Winter et al. (Proc. Soc. Exptl. Biol. N.Y. vol 111 (1962), p. 544).

DESCRIPTION OF THE PREFERRED EMBODIMENTS

The following Examples will further illustrate the invention, without limiting it thereto.

EXAMPLES

Example 1

N-(4-Carboxybenzyl)nonanamide

Methyl 4-(aminomethyl)benzoate hydrochloride (6.0 g, 0.03 moles) is treated with 50 mL 1 N NaOH and the mixture extracted with ether (3 x 50 mL). The combined ether extracts are dried with anhydrous potassium carbonate and evaporated to leave the amine base as a white solid. This residue is dissolved in 100 mL methylene chloride, to which is added 2.85 g pyridine. Nonanoyl chloride (6.36 g, 0.036 moles) in 10 mL methylene chloride is then added dropwise to the mixture with stirring over a 5 min period. The thick pasty mass which formed after a few minutes is stirred at room temperature for 45 min, at which time 30 mL saturated sodium bicarbonate is carefully added. The mixture is stirred vigorously for 15 min, after which the layers are separated and the organic layer extracted with 2 N HCl (30 mL), and dried over anhydrous sodium sulfate. Evaporation of the solvent leaves a waxy residue which is crystallized from isopropyl ether as colorless plates, m.p. 94.5°–95.5° C.

The crystalline product (2.0 g) is dissolved in tetrahydrofuran (30 mL) to which is added 1 N NaOH (10 mL). The heterogeneous mixture is stirred overnight at room temperature. The resulting clear solution is made acidic by addition of 2 N HCl, and the mixture partitioned between chloroform (250 mL) and water (200 mL). The chloroform layer is dried over sodium sulfate and evaporated to leave a waxy residue, which is crystallized as colorless needles from methanol/water. A yield of 1.36 g, of the desired product N-(4-carboxybenzyl)nonamide is obtained. M.p. 178°–179.5° C.

In a procedure analogous to that described in Example 1 above but using the appropriate acid chloride the following compounds are prepared.

Example 2

N-(4-Carboxybenzyl)decanamide sodium salt, m.p. 250° C.

Example 3

N-(4-Carboxybenzyl)heptanamide, m.p. 179°–180° C.

Example 4

N-(4-Carboxybenzyl)octanamide, m.p. 180° C.

Example 5

N-(4-Carboxybenzyl)phenylacetamide, m.p. 220°–221° C.

Example 6

N-(4-Carboxybenzyl)-4-hydroxy-3-methoxycinnamamide, m.p. 233°–234° C.

Example 7

N-(4-Carboxybenzyl)-4-phenylbutyramide 4-(Aminomethyl)benzoic acid (3.6 g) is suspended in methylene chloride (100 mL), to which 15 mL triethylamine is added. Chlorotrimethylsilane (10 mL) is then added and the mixture allowed to stir at room temperature for 1 hr. The mixture is then cooled in an ice bath and 4-phenylbutyryl chloride (5.3 g) in methylene chloride (10 mL) is added dropwise and the resulting mixture stirred for 30 min at 0° C., followed by an additional 3 hrs at ambient temperature. The mixture is treated with 75 mL 1 N HCl, after which the organic layer is separated and extracted with 1 N HCl. The precipitate which had formed is recovered by filtration and recrystallized two times from methanol/1 N HCl to give pure N-(4-carboxybenzyl)-4-phenylbutyramide M.p. 178°–179° C.

A procedure analogous to that described in Example 7 using the appropriate starting material produces the following compound:

Example 8

N-(4-Carboxybenzyl)undecanamide, m.p. 179°–180° C.

Example 9

N-(4-Carboxybenzyl)-[2-naphthoxy)acetamide (2-Naphthoxy)acetic acid (8.5 g) is suspended in 160 mL methylene chloride and treated with 1,1'-carbonyldiimidazole (6.8 g) which is added in small portions. After stirring for 3 hrs at room temperature under a nitrogen atmosphere, the mixture is added dropwise to a previously prepared solution of alpha-amino-p-toluic acid (1.4 g), chlorotrimethylsilane (10 mL), and triethylamine (11 mL) in 250 mL methylene chloride at 0° C. The final mixture is stirred at room temperature under a nitrogen atmosphere overnight. The mixture is combined with 200 mL 1 N HCl and shaken, after which the resultant precipitate is collected by suction filtration. The precipitate is recrystallized from methanol/2N HCl, m.p. 188°–189° C. as N-(4-carboxybenzyl)-(2-naphthoxy)acetamide.

Example 10

N-(4-Carboxybenzyl)cinnamamide 1,1'-Carbonyldiimidazole (3.71 9) is added to an ice-cold stirred solution of cinnamic acid (3.13 9) in 30 mL tetrahydrofuran. After stirring for an additional 1 hr, methyl 4-(aminomethyl)benzoate hydrochloride (4.7 9) and triethylamine (3.23 mL) are added and the final mixture stirred while immersed in an ice water bath for an additional 30 min, followed by stirring overnight at room temperature. After removal of the solvent by rotary evaporation, the residue is taken up in chloroform (250 mL) and extracted with water (200 mL), 1 N HCl (3×50 mL), water (100 mL), saturated sodium bicarbonate (100 mL), brine (100 mL) and the final chloroform layer dried over anhydrous magnesium sulfate. After evaporation of the solvent in vacuo, the crude product (2.74 g) is suspended in 100 mL tetrahydrofuran and 20 mL 2 N NaOH and the mixture stirred at room temperature overnight. The mixture is then made acidic by addition of excess 1 N HCl, and the precipitate recovered by filtration. After washing the filter cake with water and pressing to remove as much water as possible, the white solid is crystallized from methanol/2N HCl as N-(4-carboxybenzyl)cinnamamide, m.p. 238°–239° C.

A procedure analogous to that described in Example 10 using an appropriate starting material produces the following compound:

Example 11

N-(4-Carboxybenzyl)cyclohexylacetamide, m.p. 223°–224° C.

Example 12

N-(4-Carboxybenzyl)butyramide 4-(Aminomethyl)benzoic acid (3.0 g) is suspended in pyridine (15 mL) and the mixture cooled in an ice water bath. Butyric anhydride (9.2 mL) is added dropwise to the stirred suspension over a 20 min period. The ice bath is removed and the mixture stirred at room temperature overnight. The mixture is poured into 150 mL ice water and made acidic (pH 1.5) by addition of concentrated HCl. The precipitate is recovered by suction filtration and recrystallized from ethyl acetate to produce N-(4-carboxybenzyl)butyramide, m.p. 186.5°–187.5° C.

Example 13

N-(4-Carboxybenzyl)hexanamide

Hexanoic acid (3.06 g) in 20 mL acetonitrile is treated with N-methylmorpholine (2.9 mL) and the mixture cooled to −20° C. with stirring. Ethyl chloroformate (2.8 mL) is then added dropwise, keeping the temperature below or at −20° C. After stirring for an additional 40 min at that temperature, the solution is transferred to a cooled (−15° C.) solution of alpha-amino-p-toluic acid (2.0 g), triethylamine (15 mL), a chlorotrimethylsilane (5.0 mL) in methylene chloride (60 mL; prepared as described in Example 7). After the addition is complete, the mixture is stirred at 5° C. for hrs, followed by overnight stirring at room temperature. After removal of the solvents by evaporation, the residue is redissolved in methylene chloride (100 mL) and extracted with 1 N HCl (2×50 mL) and brine (2×50 mL). The organic layer is dried over magnesium sulfate and evaporated, leaving N-(4-carboxybenzyl)hexanamide as an off-white solid. The N-(4-carboxybenzyl)hexanamide product is crystallized from methanol/2N HCl, m.p. 178°–179° C.

Example 14

N-1-(1-(4-Carboxyphenyl)ethyl)nonanamide Step 1 4-(1-aminoethyl)benzoic acid 4-Acetylbenzoic acid (4.1 g) is dissolved in 50 mL ammonia-saturated methanol. Raney nickel catalyst (1.5 g; activity grade III) is then added and the mixture reduced under hydrogen atmosphere (4750 psi) at 80° C. for 17 hrs. After removal of the catalyst by suction filtration, the filtrate is evaporated and the residue dissolved in H$_2$O. The solution is passed through a 2.5×15 cm column of Dowex 50X8-400 resin (H+ form) and eluted with 1 N NH$_4$OH. Evaporation of the eluate leaves a residue (2.9 g) which is recrystallized from H$_2$O/acetone and characterized as 4-(1-aminothyl)benzoic acid, m.p. >300° C.

Step 2 N-1-(1-(4-Carboxyphenyl)ethyl)nonanamide

The 4-(1-aminoethyl)benzoic acid as prepared above in Step 1 (1.5 g) is suspended in 30 mL methylene chloride containing 2.13 g pyridine and cooled to 0° C. Nonanoyl chloride (1.7 g) is dissolved in 5 mL methylene chloride and added dropwise with stirring to the cooled solution. After allowing the mixture to warm to room temperature, the mixture is allowed to stir an additional 2 hrs. Treatment with 1 N HCl (40 mL) produces a solid residue at the interface of the two liquid phases, which is recovered by filtration and recrystallized from methanol/water as N-1-(1-(4-carboxyphenyl)ethyl)nonanamide, m.p. 178°–180° C.

Example 15

N-(4-carboxybenzyl)-N-methylnonanamide

Step 1 4-(methylaminomethyl)benzoic acid hydrochloride

4-Carboxybenzaldehyde (10 g) is dissolved in 50 mL aqueous methylamine (30%). Raney nickel (5 g) is added and the mixture treated with hydrogen at 1500 psi and 100° C. for 17 hrs. Removal of the catalyst by suction filtration and evaporation of the filtrate left a solid residue, which is redissolved in 2 N HCl (50 mL). The solution is extracted with ethyl acetate (50 mL) and chloroform (50 mL) and the resultant aqueous layer evaporated to dryness. The residue is vacuum dried at 60° C. for 4 hrs and recrystallized from methanol/ethyl acetate to yield 7.65 g 4-(methylaminomethyl) benzoic acid hydrochloride, m.p. 255°–261° C.

Step 2 N-(4-Carboxybenzyl-N-methylnonamide)

The 4-(methylaminomethyl)benzoic acid hydrochloride prepared in Step 1 above (2.0 g) is suspended in 5 mL pyridine and cooled in ice water. Nonanoyl chloride (1.8 g) is added dropwise with stirring, and the final solution allowed to stir at room temperature for 18 hrs. The clear solution is treated with 2 N HCl (15 mL), and partitioned between chloroform and water (50 mL each). The aqueous layer is again extracted with chloroform (25 mL) and the combined organic layers dried (Na₂SO₄) and evaporated to leave a clear viscous oil which solidifies on standing. The solid is crystallized from ethyl acetate/hexanes as N-(4-carboxybenzyl)-N-methylnonanamide, m.p. 79.5°–81° C.

Example 16

N-((4-(1H-Tetrazol-5-yl)phenyl)methyl)nonanamide

To a solution of 4-(aminomethyl)benzonitrile (5.0 g, 0.038 moles) in 100 mL chloroform is added 3.82 g (0.038 moles) triethylamine. A solution of nonanoyl chloride (6.68 g, 0.038 moles) in 10 mL chloroform is then added dropwise with stirring over a 10 min period and the final mixture stirred at room temperature for 18 hrs. The mixture is extracted with water (100 mL), saturated NaHCO₃ (50 mL), 2N HCl (50 mL), dried over Na₂SO₄ and evaporated to leave 10.2 g crude N-(4cyanobenzyl)nonanamide. This crude product is taken up in 50 mL dimethylformamide, to which is added 2.47 g (0.038 moles) sodium azide and 2.03 g (0.038 moles) ammonium chloride. The final mixture is heated at 90°–10° C. for 4 hrs after cooling, the mixture is diluted with water (350 mL) and the resultant precipitate recovered by suction filtration, washed with water, and vacuum dried. Recrystallization from ethyl acetate left N-[[4-(1H-tetrazol-5-yl)phenyl]methyl]nonanamide (2.6 g), m.p. 185°–187° C.

We claim:

1. A compound of the formula

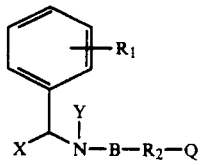

wherein:
(a) $R_1$ is COOR' wherein R' is H or lower alkyl of one to four carbons, inclusive;
(b) B is

(c) X and Y are independently H or lower alkyl of one to four carbons, inclusive;
(d) $R_2$ is alkylene, alkenylene, alkynylene branched or linear chains of 1 to 11 carbons, inclusive;
(e) Q is COOH, Br, NH₂, cyclohexyl, or

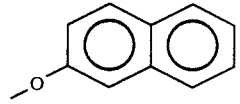

or nontoxic, pharmaceutically acceptable acid addition or base salt thereof.

2. A pharmaceutical composition comprising an effective amount of a compound of the formula:

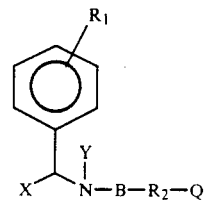

wherein
(a) $R_1$ is COOR' wherein R' is H or lower alkyl of one to four carbons, inclusive;
(b) B is

(c) X and Y are independently H or lower alkyl of one to four carbons, inclusive,
(d) $R_2$ is alkylene, alkenylene, alkynylene branched or linear chains of 1 to 11 carbons, inclusive;
(e) Q is COOH, Br, NH₂, cyclohexyl, or

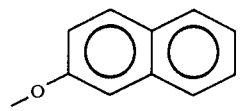

or nontoxic, pharmaceutically acceptable acid addition or base salt thereof; and a pharmaceutically acceptable carrier.

* * * * *